(12) United States Patent
Hua et al.

(10) Patent No.: US 8,889,192 B2
(45) Date of Patent: *Nov. 18, 2014

(54) MAGNETIC NANOMEDICINE FOR INHIBITING/TREATING HUMAN PROSTATE CANCER

(75) Inventors: Mu-Yi Hua, Tao-Yuan (TW); Hung-Wei Yang, Tao-Yuan (TW); Cheng-Keng Chuang, Guishan Township, Taoyuan County (TW); See-Tong Pang, Taipei (TW); Hao-Li Liu, Tao-Yuan (TW); Rung-Ywan Tsai, Kaohsiung (TW); Kun-Lung Chuang, Taipei (TW)

(73) Assignee: Chang Gung University, Tao-Yuan (TW)

( * ) Notice: Subject to any disclaimer, the term of this patent is extended or adjusted under 35 U.S.C. 154(b) by 42 days.

This patent is subject to a terminal disclaimer.

(21) Appl. No.: 13/177,034

(22) Filed: Jul. 6, 2011

(65) Prior Publication Data

US 2013/0011485 A1 Jan. 10, 2013

(51) Int. Cl.

| A61K 9/16 | (2006.01) |
| A61K 31/74 | (2006.01) |
| A61K 47/48 | (2006.01) |
| A61K 31/337 | (2006.01) |
| A61K 9/50 | (2006.01) |
| B82Y 5/00 | (2011.01) |

(52) U.S. Cl.
CPC ......... *A61K 47/48861* (2013.01); *A61K 31/337* (2013.01); *A61K 9/5094* (2013.01); *B82Y 5/00* (2013.01); *Y10S 977/773* (2013.01); *Y10S 977/788* (2013.01); *Y10S 977/906* (2013.01)
USPC ........ 424/497; 424/78.08; 977/773; 977/788; 977/906

(58) Field of Classification Search
CPC .................... C08G 73/0266; A61K 47/48861; A61K 9/5094; A61K 31/337; B82Y 5/00
USPC ............... 424/497, 78.08; 977/773, 788, 906; 532/176

See application file for complete search history.

(56) References Cited

U.S. PATENT DOCUMENTS 5,932,144 A * 8/1999 Shimizu et al. ............... 252/500
8,329,222 B1 * 12/2012 Hua et al. ...................... 424/489

(Continued)

OTHER PUBLICATIONS

Shchukin et al. (Micron-scale hollow polyelectrolyte capsules with nanosized magnetic Fe3O4 inside, Materials Letters 57 (2003) 1743-1747), 5 pages.*

(Continued)

*Primary Examiner* — Jason Sims
*Assistant Examiner* — Miriam A Levin
(74) *Attorney, Agent, or Firm* — Muncy, Geissler, Olds & Lowe, P.C.

(57) ABSTRACT

The present invention discloses a magnetic nanomedicine for inhibiting/treating human prostate cancer, which comprises a core containing a magnetic particle having a diameter of less than 10 nm; a shell made of a carboxylated polyaniline and encapsulating the core; and a medicine covalently linked to the shell and able to inhibit/treat prostate cancer. The magnetic nanomedicine of the present invention not only has superior thermal stability and but also has water solubility higher than that of the conventional anti-prostate cancer medicine. Further, the magnetic nanomedicine of the present invention can be magnetically conducted to the cancer area to increase the local concentration of medicine and enhance the therapeutic effect.

6 Claims, 12 Drawing Sheets
(9 of 12 Drawing Sheet(s) Filed in Color)

(56) References Cited

U.S. PATENT DOCUMENTS

| | | | |
|---|---|---|---|
| 2005/0129727 A1* | 6/2005 | Weber et al. | 424/423 |
| 2011/0104077 A1* | 5/2011 | Hua et al. | 424/9.323 |
| 2011/0104294 A1* | 5/2011 | Hua et al. | 424/497 |
| 2012/0095325 A1* | 4/2012 | Wei et al. | 600/411 |

OTHER PUBLICATIONS

Yang et al. (A new drug of BCNU bound on magnetic nano-particles and their in vitro antitumor activity against Glioma C6 cells, poster, 2009 IEEE International Magnetics Conference; cited in Office Action for copending U.S. Appl. No. 12/799,893), 2 pages.*

Hua et al. (Magnetic-nanoparticle-modified paclitaxel for targeted therapy for prostate cancer, Biomaterials (2010) 31:7355-7363; published on-line Jul. 6, 2010), 9 pages.*

Chemoth (Types of Chemotherapy Agents and Regimens, The Chemotherapy Drug Industry [Retrieved from internet <URL: http://chemoth.com/economics >] [Downloaded Jan. 25, 2014]), 4 pages.*

Koziara et al. (Paclitaxel nanoparticles for the potential treatment of brain tumors, Journal of Controlled Release (2004) 99: 259-269), 11 pages.*

CN 102058605 A (pub. May 18, 2011; machine translation), 5 pages.*

CN 101991861 A (pub. May 18, 2011; machine translation), 8 pages.*

F. Danhier et al., "Novel self-assembling PEG-p-(CL-*co*-TMC) polymeric micelles as safe and effective delivery system for Paclitaxel" *European Journal of Pharmaceutics and Biopharmaceutics* 73 (2009) pp. 230-238.

K. Xiao et al., "A self-assembling nanoparticle for paclitaxel delivery in ovarian cancer" *Biomaterials* 30 (2009) pp. 6006-6016.

E. Bilensoy et al., "Development of Nonsurfactant Cyclodextrin Nanoparticles Loaded with Anticancer Drug Paclitaxel" *Journal of Pharmaceutical Sciences*, vol. 97, No. 4, Apr. 2008, pp. 1519-1529.

M. Hua et al., "Magnetic-nanoparticle-modified paclitaxel for targeted therapy for prostate cancer" *Biomaterials* 31 (2010) pp. 7355-7363.

* cited by examiner

(■)PC-3 cell and (b) CWR22R cell. Control;
(●)SPAnH/MNPs composites;
(▲)SPAnH/NMPs composites with external magnetic field of 800 Gauss;
(▼)10 μM free Taxol;
(◄)10 μM effective bound Taxol; and
(◆)10 μM effective bound Taxol with external magnetic field of 800 Gauss.

MAGNETIC NANOMEDICINE FOR INHIBITING/TREATING HUMAN PROSTATE CANCER

BACKGROUND OF THE INVENTION

1. Field of the Invention

The present invention relates to a magnetic nanomedicine for inhibiting/treating human prostate cancer, particularly to a magnetic nanomedicine, whose local concentration can be magnetically promoted to inhibit/treat prostate cancer without using surgical operation.

2. Description of the Related Art

At present, the prostate cancer is primarily treated with Taxol and the derivatives thereof. However, Taxol is poisonous and water-insoluble. Thus, Taxol injection and treatment has many side-effects. The current solution is carrying Taxol with a vector system to the nidus and releasing Taxol in the nidus.

The current vector technologies include the liposome encapsulation method, the transistor encapsulation method, the gelatin encapsulation method, the polymer vesicle system, and the magnetic nanocomposite method wherein the medicine is encapsulated by a compatible polymeric material. In the liposome encapsulation method, medicine is encapsulated by liposome, whereby the medicine can be released gradually and exempted from being decomposed by enzymes in the digestive tract. However, the timing and dose of releasing medicine are hard to accurately calculate in the liposome technology. In the transistor encapsulation method, a transistor encapsulating medicine is surgically implanted into the cancer area and then releases the medicine to the cancer to effectively increase the medicine concentration in the cancer with the normal regions being less affected by the medicine. In the gelatin encapsulation method, gelatin encapsulates magnetic particles and medicine, and the package is magnetically conducted to the nidus. However, the package has too greater a diameter (about 150-350 nm). Besides, the medicine releasing rate is hard to accurately control in the gelatin encapsulation method. The polymer vesicle system can gradually release medicine to increase the time that the medicine remains in the body. However, the polymer vesicle system cannot concentrate the medicine to the cancer area.

SUMMARY OF THE INVENTION

In order to solve the problems of the current medicine vector technologies and overcome the side effects of anti-prostate cancer medicine, the Inventors devote themselves to research and experiment and finally invent a magnetic nanomedicine for inhibiting/treating human prostate cancer.

The present invention provides a magnetic nanomedicine, which is free of surfactants, dispersing agents and crosslinking agents, and which can increase thermal stability and water-solubility and decrease the biological rejection for Taxol and the derivatives thereof, and which can be magnetically conducted to the cancer area without using surgical operation, enhancing the therapeutic effect.

To achieve the abovementioned objectives, the present invention proposes a magnetic nanomedicine for inhibiting/treating human prostate cancer, which comprises a core containing a magnetic particle with a diameter less than 10 nm; a shell made of carboxylated polyaniline and encapsulating the core; a medicine covalently linked to the shell and able to inhibit/treat prostate cancer.

The present invention can obviously improve the thermal stability of Taxol—a conventional medicine for treating prostate cancer. At a temperature of 37° C., the present invention prolongs the half life of Taxol from 19 hours to 57 hours. After being stored at a temperature of 25° C. for 14 days, the conventional Taxol has lost its activity. However, the magnetic nanomedicine of the present invention still possesses 29% activity after being stored at a temperature of 25° C. for 21 days. Therefore, the storage stability of the medicine of the present invention is much superior to that of the conventional Taxol. Further, the present invention greatly improves the water-insolubility of the conventional Taxol, and the magnetic nanomedicine of the present invention can be uniformly dispersed in water. Furthermore, the magnetic nanomedicine of the present invention has superparamagnetism and can be conducted to a specialized area by an external magnetic field to locally increase the medicine concentration. In-vitro toxicity tests show that a 10 μM effective concentration of medicine together with an 800-Gauss magnetic field can poisonously kill the human prostate cancer cells PC3 and CWR22R more effectively than the conventional Taxol. The magnetic nanomedicine of the present invention outperforms the conventional Taxol respectively by 30% and 47% in the efficiencies of inhibiting human prostate cancer cells PC3 and CWR22R.

BRIEF DESCRIPTION OF DRAWINGS AND APPENDIXES

The patent or application file contains at least one drawing executed in color. Copies of this patent or patent application publication with color drawing(s) will be provided by the Office upon request and payment of the necessary fee.

DETAILED DESCRIPTION OF THE INVENTION

Below, embodiments are described in detail to demonstrate the present invention.

Embodiment I

Using a Co-Deposition Method to Fabricate Ferric Ferrous Oxide Magnetic Nanoparticles ($Fe_3O_4$(MNPs))

Firstly, add 0.7 g iron trichloride ($FeCl_3$) ($4.32 \times 10^{-3}$ mole), 1.07 g tetrahydrate ferrous chloride ($FeCl_2 \cdot 4H_2O$)($6.48 \times 10^{-3}$ mole) and 400 ml of double distilled water into a three-necked bottle and agitate it at an ambient temperature and in a nitrogen environment for 5 minutes to completely dissolve $FeCl_3$ and $FeCl_2 \cdot 4H_2O$ in water. Next, add 20 mL of 0.864N sodium hydroxide (NaOH) aqueous solution into the three-necked bottle, and raise the temperature of the solution to 80° C., whereby an aqueous solution containing MNPs is formed. Next, after the MNPs-containing aqueous solution cools down, ultrasonically vibrate the MNPs-containing aqueous solution to uniformly disperse MNPs in the aqueous solution. Next, pour the MNPs-containing aqueous solution into a separating funnel, and place a strong magnet outside the funnel to attract MNPs with the aqueous solution flowing away from the bottom of the funnel, whereby MNPs are separated from the solution. Next, use double distilled water to flush MNPs repeatedly until the solution flowing away from the bottom of the funnel is neutralized and colorless.

Figure 1A:
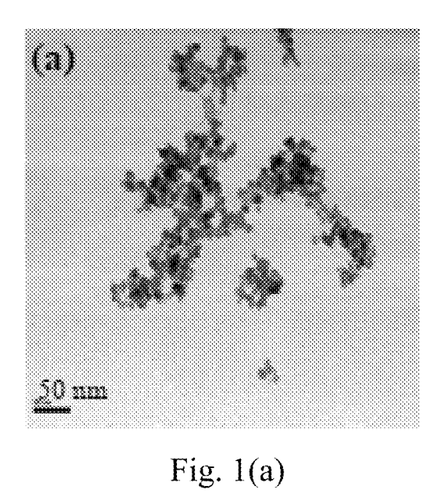
FIG. 1(a) shows a TEM photograph of magnetic nanoparticles according to one embodiment of the present invention.
Figure 2:
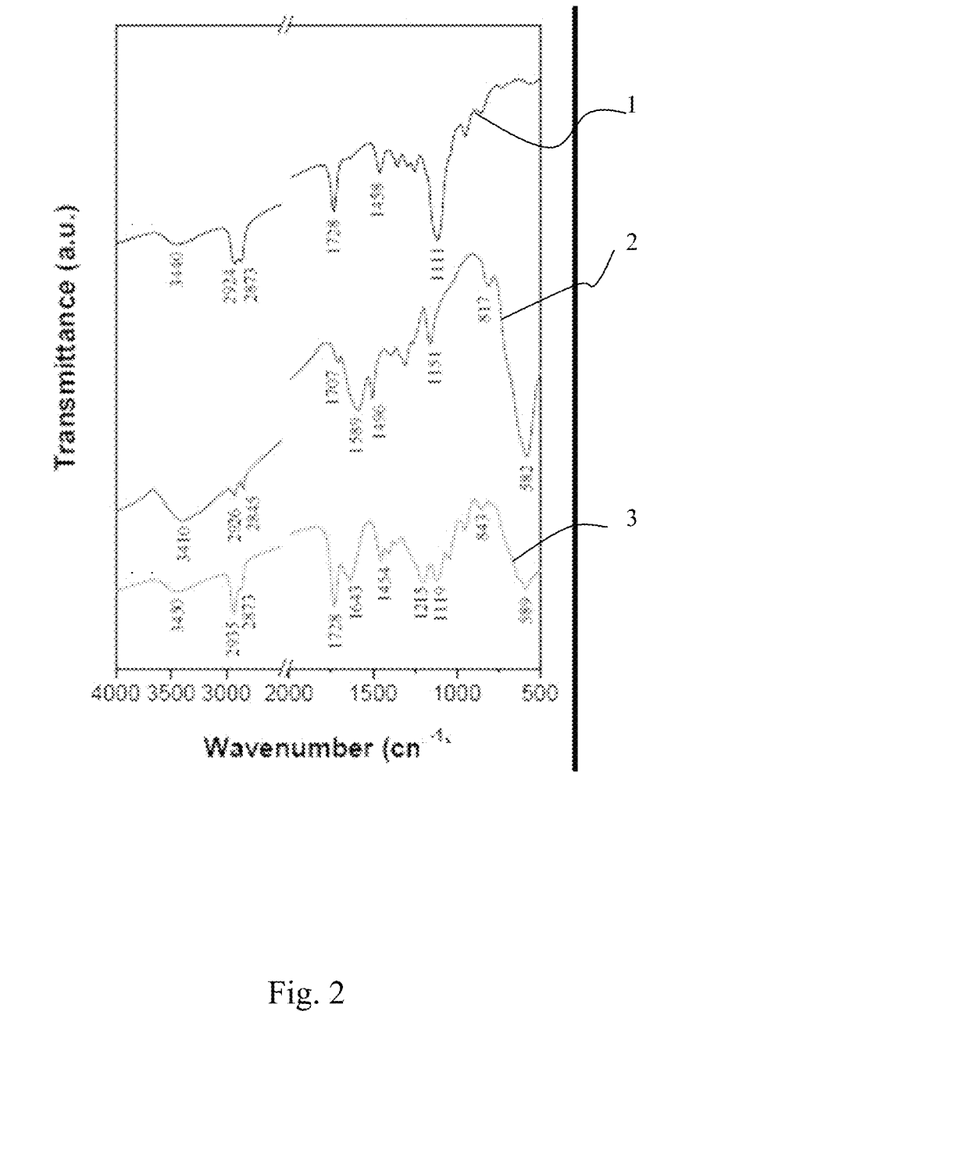
FIG. 2 shows the infrared spectra of MNPs, the SPAnH/MNPs magnetic nanocomposite and the SPAnH/MNPs/Taxol magnetic nanomedicine according to one embodiment of the present invention.
Figure 3:
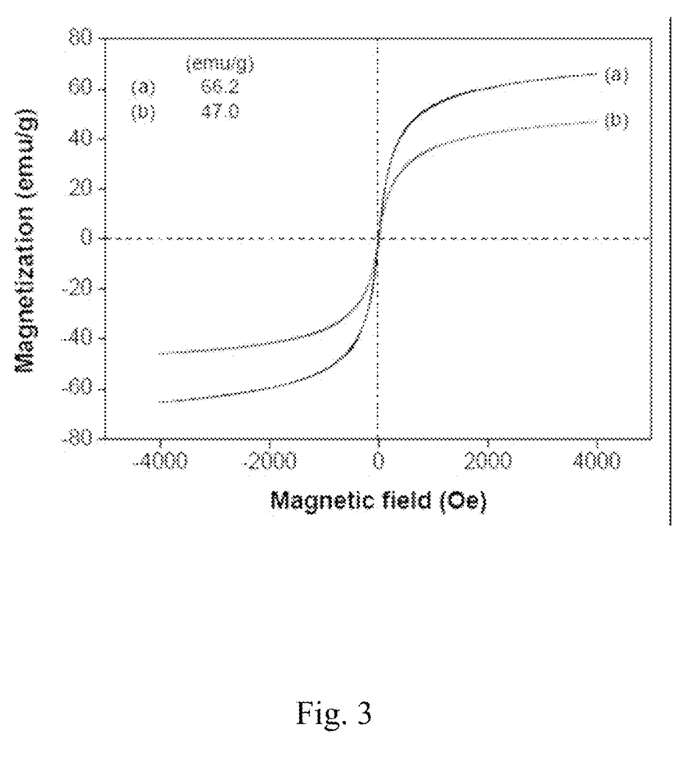
FIG. 3 shows the magnetic hysteresis curves of MNPs and the SPAnH/MNPs magnetic nanocomposite at an ambient temperature according to one embodiment of the present invention.

From the transmission electron microscope (TEM) photograph in FIG. 1(a), it is observed that the MNPs have a particle size of about 8 nm. Curve 1 in FIG. 2 is an infrared spectrum of MNPs. The Fe—O ($\nu_{Fe-O}$) stretching vibration of MNPs appears at 587 cm$^{-1}$. Curve (a) in FIG. 3 is an MNPs magnetic hysteresis curve obtained with SQUID (Superconducting Quantum Interference Device). The saturation magnetization of MNPs is found to be 66.2 emu/g. Normally, the saturation magnetization of MNPs increases with the magnetic field, and the magnetization curve passes through the origin, wherefore the MNPs of the present invention has the feature of superparamagnetism.

Embodiment II

A Method for Fabricating a SPAnH/MNPs Magnetic Nanocomposite

Firstly, mix 5 ml of an MNPs aqueous solution having a concentration of 6.4 mg/mL and 1.5 ml of an SPAnNa (poly[aniline-co-sodium N-(1-one-butyric acid) aniline]) aqueous solution having a concentration of 5.5 mg/mL uniformly to form a mixed solution. Next, ultrasonically vibrate the mixed solution, and drop 0.5M hydrochloric acid (HCl) solution into the mixed solution. In an acidic environment, SPAnNa aggregates to form SPAnH (Poly[aniline-co-N-(1-one-butyric acid)]aniline), and SPAnH envelops MNPs to form a magnetic nanocomposite with the core being MNPs and the shell being SPAnH. Next, separate the magnetic nanocomposite from the solution and then disperse the magnetic nanocomposite in double distilled water. Thus is formed a SPAnH/MNPs magnetic nanocomposite.

Figure 1B:
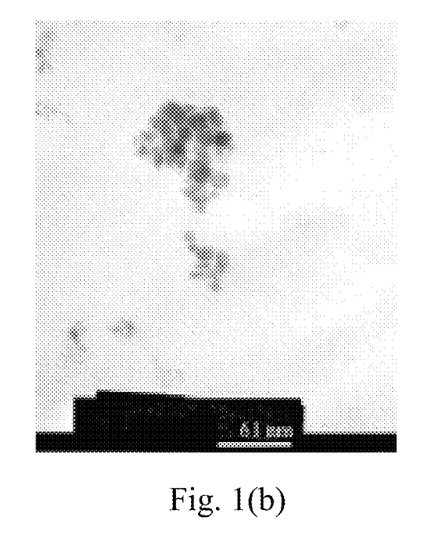
FIG. 1(b) shows a TEM photograph of a magnetic nanocomposite containing MNPs and a carboxylated polyaniline shell encapsulating MNPs according to one embodiment of the present invention.

From the TEM photograph in FIG. 1(b), it is observed that the SPAnH/MNPs magnetic nanocomposite has a particle size of about 15 nm. Curve 2 in FIG. 2 is an infrared spectrum of the SPAnH/MNPs magnetic nanocomposite. In the infrared spectrum of the SPAnH/MNPs magnetic nanocomposite, there is also a Fe—O ($\nu_{Fe-O}$) stretching vibration appearing at 582 cm$^{-1}$; there are a saturation-symmetric stretching vibration and a saturation-asymmetric stretching vibration of C—H ($\nu_{C-H}$) respectively appearing at 2844 cm$^{-1}$ and 2927 cm$^{-1}$; and there are a C=O ($\nu_{C=O}$) stretching vibration and an O—H ($\nu_{O-H}$) stretching vibration of the functional group —COOH respectively appearing at 1797 cm$^{-1}$ and 3410 cm$^{-1}$. The abovementioned stretching vibrations, indicate that MNPs is indeed enveloped by a layer of SPAnH. Curve (b) in FIG. 3 is a SPAnH/MNPs magnetic hysteresis curve obtained with SQUID. From Curve (b) of FIG. 3, it is found that the SPAnH/MNPs magnetic nanocomposite of the present invention has superparamagnetism with a saturation magnetization of 47.0 emu/g.

Embodiment III

Figure 8:
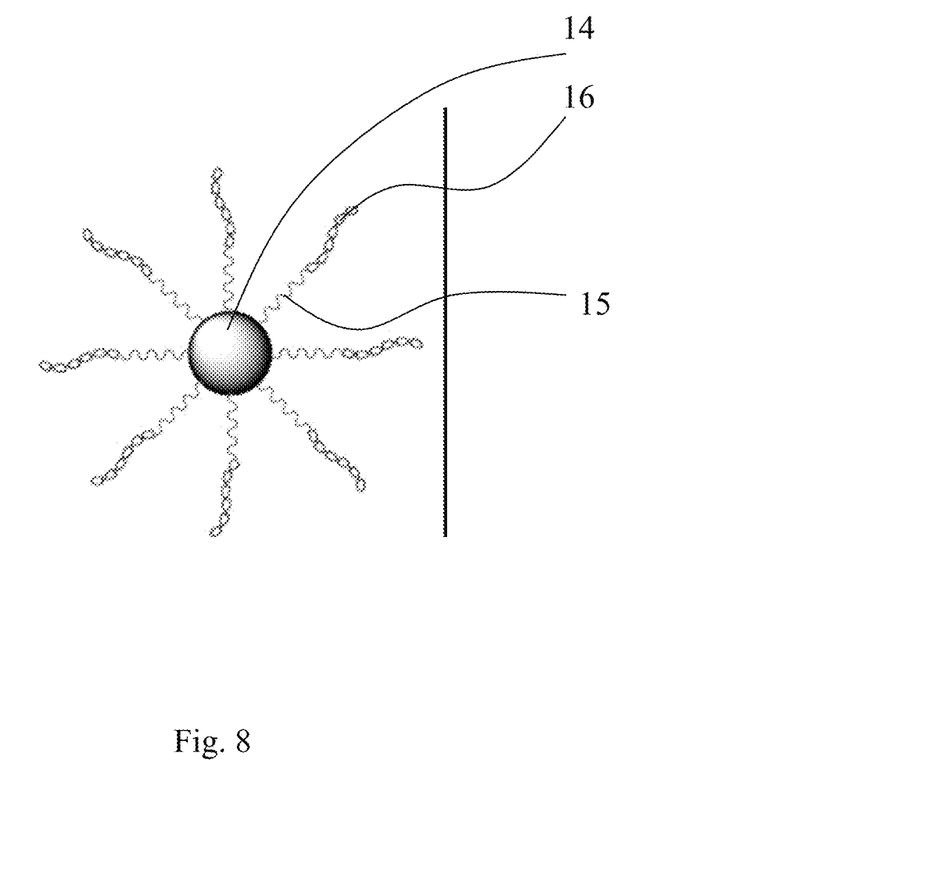
FIG. 8 is a diagram schematically showing the structure of a magnetic nanomedicine according to one embodiment of the present invention.

Effect of Bonding a Higher Concentration Taxol to the SPAnH/MNPs Magnetic Nanocomposite Dissolve 24 mg of EDC (1-ethyl-3-(3-dimethylaminepropyl) carbodiimide hydrochloride) and 27 mg of sulfo-NHS (N-hydroxysulfosuccinimide sodium salt) in 0.5M MES buffer (2-Morpholinoethanesulfonic acid, pH=6.3) to form a mixed solution. Next, take 0.2 mL of the mixed solution to react with 0.2 mL of SPAnH/MNPs for 30 minutes and then flush the product with the MES buffer. Next, add 500 μg of Taxol to the product to undertake a bonding reaction at a reaction temperature of 15-20° C. to form a SPAnH/MNPs/Taxol magnetic nanomedicine. Next, flush off free Taxol with ethyl alcohol and deionized water to form the SPAnH/MNPs/Taxol magnetic nanomedicine shown in FIG. 8.

Figure 4:
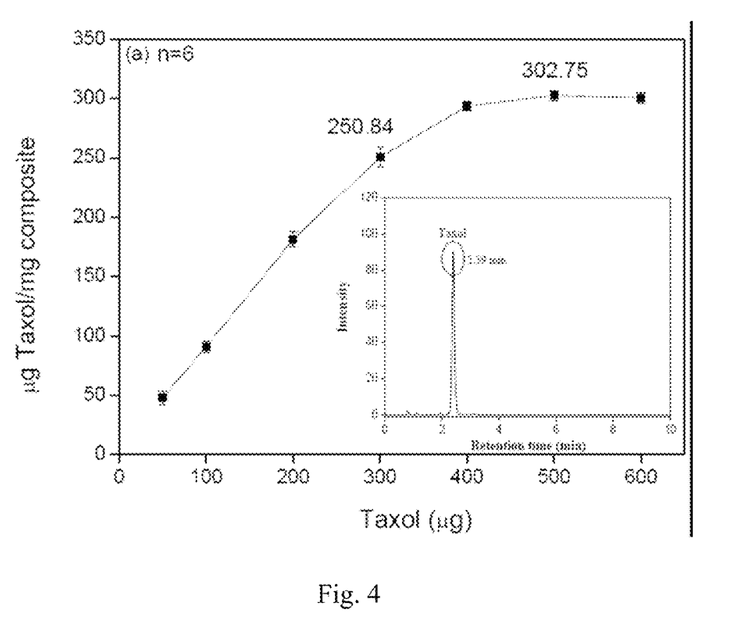
FIG. 4 shows the efficiency of bonding Taxol to SPAnH/MNPs, wherein the interior diagram shows HPLC of Taxol.

Determine the quantity of the flushed-off free Taxol with HPLC (High Performance Liquid Chromatography) under the conditions of using a solution of alcohol/water (v/v) 60/40, a flow rate of 2 mL/min and a detected wavelength of 227 nm. Work out the quantity of Taxol bound to SPAnH/MNPs magnetic nanocomposite from the quantity of the free Taxol. As shown in FIG. 4, the quantity of Taxol bound to SPAnH/MNPs magnetic nanocomposite is 302.75 μg, and the activity of the SPAnH/MNPs/Taxol magnetic nanomedicine is 50.3%. FIG. 4 shows that a high concentration of Taxol appears at a retention time of 2.38 minutes.

Embodiment IV

Effect of Bonding a Lower Concentration Taxol to the SPAnH/MNPs Magnetic Nanocomposite Dissolve 24 mg of EDC and 27 mg of sulfo-NHS in 0.5M MES buffer (pH=6.3) to form a mixed solution. Next, take 0.2 mL of the mixed solution to react with 0.2 mL of SPAnH/MNPs for 30 minutes and then flush the product with 0.1M MES buffer. Next, add 300 μg of Taxol to the product to undertake a bonding reaction at a reaction temperature of 15-20° C. for 2 hours to form a SPAnH/MNPs/Taxol magnetic nanomedicine. Next, flush off free Taxol with ethyl alcohol and deionized water. Determine the quantity of the flushed-off free Taxol with HPLC under the conditions of using a solution of alcohol/water (v/v) 60/40, a flow rate of 2 mL/min and a detected wavelength of 227 nm. Work out the quantity of Taxol bound to SPAnH/MNPs magnetic nanocomposite from the quantity of the free Taxol. As shown in FIG. 4, the quantity of Taxol bound to SPAnH/MNPs magnetic nanocomposite is 250.84 μg, and the activity of the SPAnH/MNPs/Taxol magnetic nanomedicine is 78.4%.

Curve 3 in FIG. 2 is an infrared spectrum of the SPAnH/MNPs/Taxol magnetic nanomedicine. In the infrared spectrum of the SPAnH/MNPs/Taxol magnetic nanomedicine, there is also a Fe—O ($v_{Fe-O}$) stretching vibration appearing at 589 cm$^{-1}$; there are a saturation-symmetric stretching vibration and a saturation-asymmetric stretching vibration of C—H ($v_{C-H}$) respectively appearing at 2873 cm$^{-1}$ and 2935 cm$^{-1}$; there is a stretching vibration of C=O ($v_{N-C=O}$) of amide at 1643 cm$^{-1}$, wherein the C=O belongs to an amido functional group formed via covalently integrating COOH and NH; there is a stretching vibration of C—O—C ($v_{C-O-C}$) appearing at 1111 cm$^{-1}$, wherein the C—O—C belongs to an aldehyde functional group; there is a stretching vibration of C=O ($v_{C=O}$) appearing at 1728 cm$^{-1}$, wherein the C=O belongs to a ketone functional group. The abovementioned stretching vibrations indicate that Taxol is indeed bound to the SPAnH/MNPs magnetic nanocomposite.

Embodiment V

Stability Analysis of the SPAnH/MNPs/Taxol Magnetic Nanomedicine

Figure 5A:
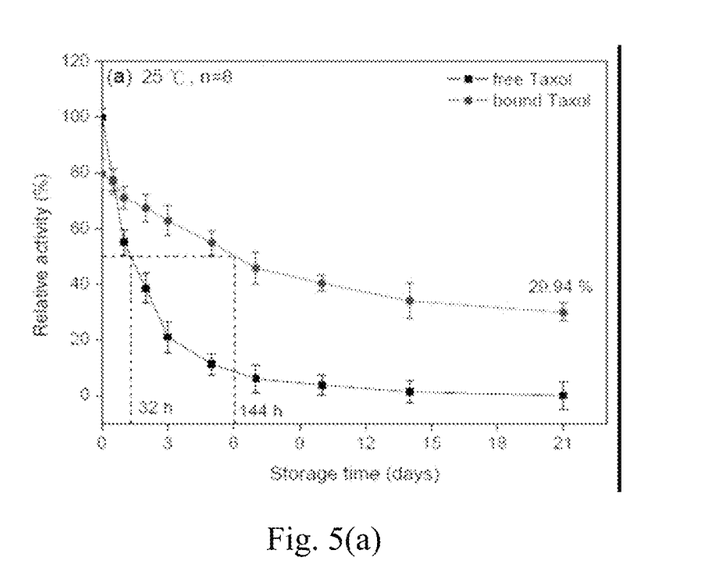
FIG. 5(a) shows the stabilities of Taxol and the magnetic nanomedicine at a temperature of 25° C. according to one embodiment of the present invention.
Figure 5B:
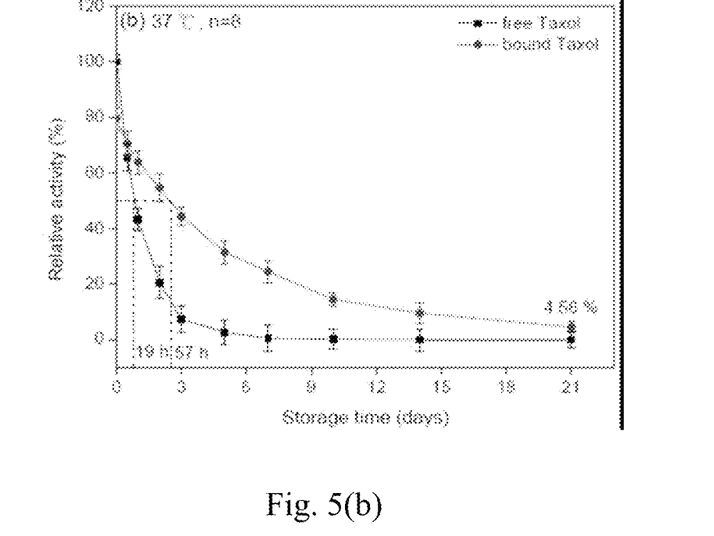
FIG. 5(b) shows the stabilities of Taxol and the magnetic nanomedicine at a temperature of 37° C. according to one embodiment of the present invention.

Store the SPAnH/MNPs/Taxol magnetic nanomedicine respectively at temperatures of 4° C., 25° C. and 37° C. Use the tubulin protein assay to detect the residual activities of the SPAnH/MNPs/Taxol magnetic nanomedicine after it has been stored for 1-21 so as to compare the storage stabilities. Normally, the conventional Taxol has a half life of 32 hours at a temperature of 25° C. and a half life of 19 hours at a temperature of 37° C. Refer to FIG. 5(a) and FIG. 5(b), the SPAnH/MNPs/Taxol magnetic nanomedicine of the present invention has a half life of 144 hours at a temperature of 25° C. and a half life of 57 hours at a temperature of 37° C. The experiment proves that the present invention can decrease the deactivation speed of Taxol and increase the stability of Taxol.

Embodiment VI

The Influence of the SPAnH/MNPs/Taxol Magnetic Nanomedicine on Growth of the Human Prostate Cancer Cells PC3

Cell cultivation: Place 150 μL of a mixture liquid containing 10000 human prostate cancer cells PC3 into every well of a 96-well culture plate. Place the culture plates in a humidified incubator at a temperature of 37 C.° and with 5% $CO_2$ to enable adherent growth of the cells.

Agent addition: 24 hours later, separately mix SPAnH/MNPs magnetic nanocomposite (600 μg/mL), Taxol, and SPAnH/MNPs/Taxol magnetic nanomedicine with a RPMI1640 medium to form mixed solutions. Respectively add 50 μL of the mixed solutions to every well, whereby SPAnH/MNPs, Taxol, and SPAnH/MNPs/Taxol respectively have final concentrations of 2, 5 and 10 μM in the wells. Place the culture plates in a humidified incubator at a temperature of 37 C.° and with 5% $CO_2$. Count the numbers of cells to evaluate growth of the cells 2, 4, 6, 8, 24, and 48 hours later.

Cell counting: Remove RPMI1640 and add 120 μL of an XTT reaction liquid (2,3-Bis(2-methoxy-4-nitro-5-sulfophenyl)-2H-tetrazolium-5-carboxanilide inner salt) to the wells. Use an ELISA reader (BIO-TEK, model EL 808) to measure the OD (Optical Density) values at a wavelength of 490 nm to estimate the toxicity of SPAnH/MNPs and the cell-killing rate of SPAnH/MNPs/Taxol to the PC3 cancer cells.

Figure 6A:
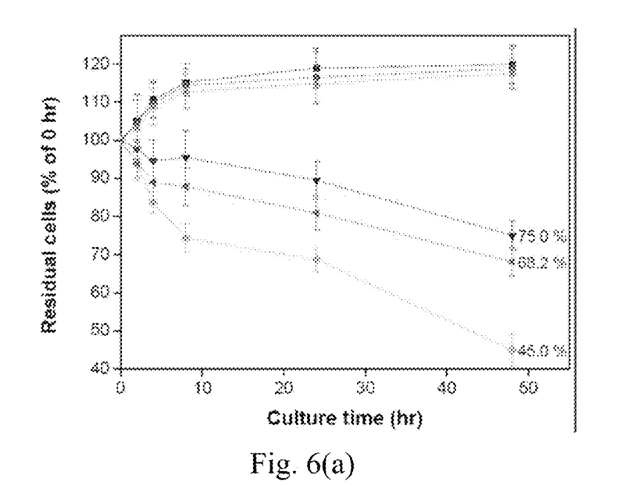
FIG. 6(a) shows the influences of different medicines on growth of PC3 prostate cancer cells.

Test results: As shown in FIG. 6(a), SPAnH/MNPs do not show any toxicity to PC3 cancer cells after PC3 cancer cells have been cultivated together with SPAnH/MNPs for 48 hours. Even when a magnetic field is applied to move SPAnH/MNPs to PC3 cancer cells, PC3 cancer cells are not poisoned by SPAnH/MNPs either. 2 μM and 5 μM of the SPAnH/MNPs/Taxol magnetic nanomedicine do not inhibit growth of PC3 cancer cells. Even when a magnetic field is applied to move the SPAnH/MNPs/Taxol magnetic nanomedicine to PC3 cancer cells, 2 μM of the SPAnH/MNPs/Taxol cannot inhibit growth of PC3 cancer cells either. When PC3 cancer cells have been cultivated with 5 μM of SPAnH/MNPs/Taxol for 48 hours under a magnetic field, about 9% of cell growth is inhibited. However, most cells are not killed by 5 μM of SPAnH/MNPs/Taxol. In the cases that 10 μM of Taxol and 10 μM of SPAnH/MNPs/Taxol are added, the PC3 growth-inhibition ratios are respectively 25% and 32% 48 hours later. When an external magnetic field (800 Gauss) is applied to the culture plates where PC3 cancer cells are cultivated with 10 μM of SPAnH/MNPs/Taxol, the PC3 growth-inhibition ratio is increased to as high as 55%. The magnetic field can guide SPAnH/MNPs/Taxol to concentrate around PC3 cancer cells. Thus, PC3 cancer cells are fed with more medicine and poisoned more seriously.

Embodiment VII

The Influence of the SPAnH/MNPs/Taxol Magnetic Nanomedicine on Growth of the Human Prostate Cancer Cells CWR22R Cell cultivation: Place 150 μL of a mixture liquid containing 10000 human prostate cancer cells CWR22R into every well of a 96-well culture plate. Place the culture plates in a humidified incubator at a temperature of 37° C.° and with 5% $CO_2$ to enable adherent growth of the cells.

Agent addition: 24 hours later, separately mix SPAnH/MNPs magnetic nanocomposite (600 μg/mL), Taxol, and SPAnH/MNPs/Taxol magnetic nanomedicine with a RPMI1640 medium to form mixed solutions. Respectively add 50 μL of the mixed solutions to every well, whereby SPAnH/MNPs, Taxol, and SPAnH/MNPs/Taxol respectively have final concentrations of 2, 5 and 10 μM in the wells. Place the culture plates in a humidified incubator at a temperature of 37 C.° and with 5% $CO_2$. Count the numbers of cells to evaluate growth of the cells 2, 4, 6, 8, 24, and 48 hours later.

Cell counting: Remove RPMI1640 and add 120 μL of an XTT reaction liquid to the wells. Use an ELISA reader (BIO-TEK, model EL 808) to measure the OD (Optical Density) values at a wavelength of 490 nm to estimate the toxicity of SPAnH/MNPs and the cell-killing rate of SPAnH/MNPs/Taxol to the CWR22R cancer cells.

Figure 6B:
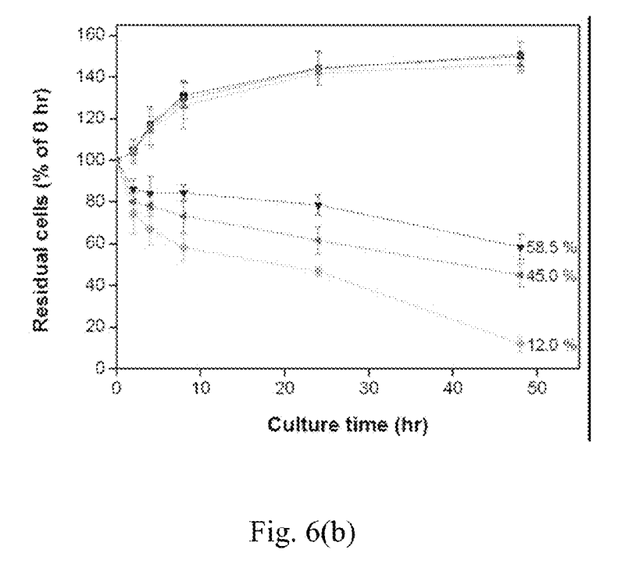
FIG. 6(b) shows the influences of different medicines on growth CWR22R prostate cancer cells.

Test results: As shown in FIG. 6(b), SPAnH/MNPs do not show any toxicity to CWR22R cancer cells after CWR22R cancer cells have been cultivated together with SPAnH/MNPs for 48 hours. Even when a magnetic field is applied to move SPAnH/MNPs to CWR22R cancer cells, CWR22R cancer cells are not poisoned by SPAnH/MNPs either. In the cases that 2 μM and 5 μM of SPAnH/MNPs/Taxol are added to the culture plates with a magnetic field applied to the culture plates, they can inhibit growth of CWR22R cancer cells for 48 hours, and the growth-inhibition ratios thereof are respectively 2% and 26%. In the cases that 10 μM of Taxol and 10 μM of SPAnH/MNPs/Taxol are added to the culture plates, the growth-inhibition ratios thereof are respectively increased to as high as 41% and 55% 48 hours later. When an external magnetic field (800 Gauss) is applied to the culture plates where CWR22R cancer cells are cultivated with 10 μM of SPAnH/MNPs/Taxol, the CWR22R growth-inhibition ratio is increased to as high as 88%. The magnetic field can guide SPAnH/MNPs/Taxol to concentrate around CWR22R cancer cells. Thus, CWR22R cancer cells are fed with more medicine and poisoned more seriously.

Embodiment VIII

The Influence of the SPAnH/MNPs/Taxol Magnetic Nanomedicine on the Human Prostate Cancer Cells PC3

Add 2 mL of a mixture liquid containing 20000 PC3 cancer cells to 3.5 cm-diameter culture plates. Place the culture plates in a humidified incubator at a temperature of 37° C.° and with 5% $CO_2$ to enable adherent growth of the cells. Twenty-four hours later, add to the culture plates the mixture solutions respectively formed via mixing the RPMI1640 medium with the SPAnH/MNPs magnetic nanocomposite and 2, 5, 10 μM of SPAnH/MNPs/Taxol magnetic nanomedicine. Continue to cultivate PC3 cancer cells. Eight hours later, flush the contents of the culture plates with 1 mL of HBSS (Hanks' Balance Slat Solution).

Figure 9:
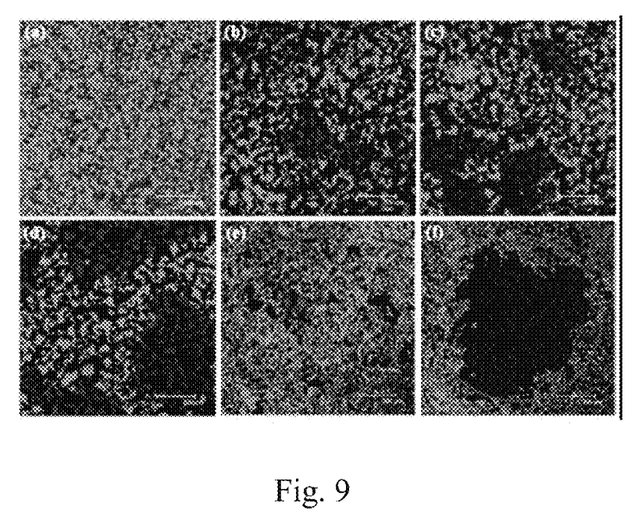
FIG. 9 shows the fluorescent microscopic images for evaluating the toxicity of the magnetic nanomedicine of the present invention to PC3 prostate cancer cells.

FIG. 9 shows the fluorescent microscopic images of PC3 cancer cells. It is found: the higher the concentration of the SPAnH/MNPs/Taxol magnetic nanomedicine, the more the red fluorescent spots that mark dead PC3 cancer cells. This means that 10 μM of SPAnH/MNPs/Taxol can kill more PC3 cancer cells than 2 or 5 μM of SPAnH/MNPs/Taxol. Such a result matches the growth curve of the cells.

Refer to FIG. 9(f), wherein the area that a magnetic field is applied to is designated by a red circle. It is found that most SPAnH/MNPs/Taxol magnetic medicine is attracted to the specified area. Thus, cells are massively killed in the specified area. The SPAnH/MNPs/Taxol magnetic medicine is impoverished outside the specified area. Therefore, a great number of green fluorescent spots that mark live cells appear in the region where SPAnH/MNPs/Taxol is impoverished. The result proves that a magnetic field can guide SPAnH/MNPs/Taxol to a specified area to increase the local concentration of medicine.

Embodiment IX

The Influence of the SPAnH/MNPs/Taxol Magnetic Nanomedicine on the Human Prostate Cancer Cells CWR22R Add 2 mL of a mixture liquid containing 20000 CWR22R cancer cells to 3.5 cm-diameter culture plates. Place the culture plates in a humidified incubator at a temperature of 37° C.° and with 5% $CO_2$ to enable adherent growth of the cells. Twenty-four hours later, add to the culture plates the mixture solutions respectively formed via mixing the RPMI1640 medium with the SPAnH/MNPs magnetic nanocomposite and 2, 5, 10 μM of SPAnH/MNPs/Taxol magnetic nanomedicine. Continue to cultivate CWR22R cancer cells. Eight hours later, flush the contents of the culture plates with 1 mL of HBSS (Hanks' Balance Slat Solution).

Figure 10:
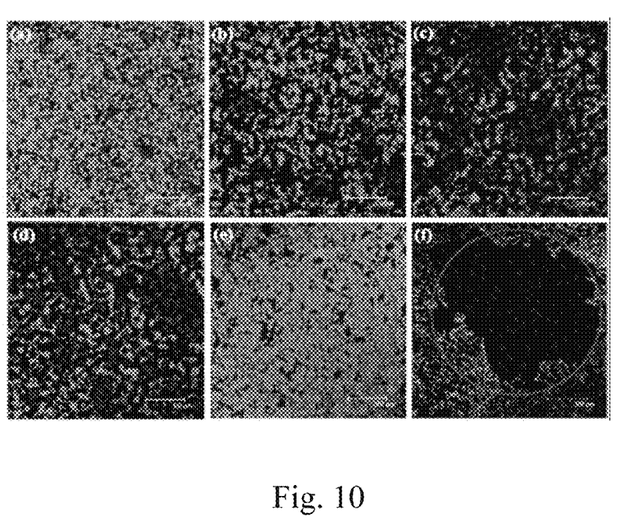
FIG. 10 shows the fluorescent microscopic images for evaluating the toxicity of the magnetic nanomedicine of the present invention to CWR22R prostate cancer cells.

FIG. 10 shows the fluorescent microscopic images of CWR22R cancer cells. It is found: the higher the concentration of the SPAnH/MNPs/Taxol magnetic nanomedicine, the more the red fluorescent spots that mark dead CWR22R cancer cells. This means that 10 μM of SPAnH/MNPs/Taxol can kill more CWR22R cancer cells than 2 or 5 μM of SPAnH/MNPs/Taxol. Such a result matches the growth curve of the cells.

Refer to FIG. 10(f), wherein the area that a magnetic field is applied to is designated by a red circle. It is found that most SPAnH/MNPs/Taxol magnetic medicine is attracted to the specified area. Thus, cells are massively killed in the specified area. The SPAnH/MNPs/Taxol magnetic medicine is impoverished outside the specified area. Therefore, a great number of green fluorescent spots that mark live cells appear in the region where SPAnH/MNPs/Taxol is impoverished. The result proves that a magnetic field can guide SPAnH/MNPs/Taxol to a specified area to increase the local concentration of medicine.

Embodiment X

Figure 1C:
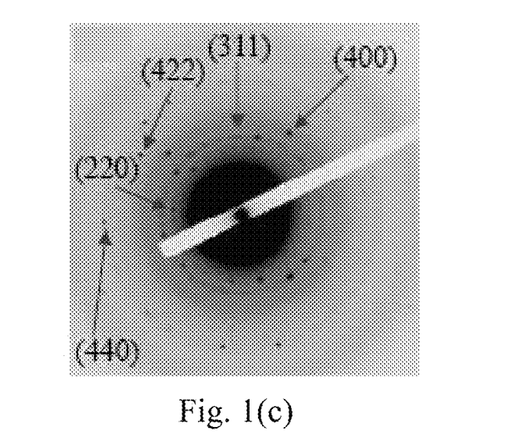
FIG. 1(c) shows an electron diffraction pattern of a magnetic nanocomposite containing MNPs and a carboxylated polyaniline shell encapsulating MNPs according to one embodiment of the present invention.

The Crystallographic Structure of the SPAnH/MNPs/Taxol Magnetic Nanomedicine in PC3 Cancer Cells Respectively cultivate PC3 cancer cells together with the SPAnH/MNPs nanocomposite and the SPAnH/MNPs/Taxol magnetic nanomedicine for 2 hours. Slice the samples Use TEM (Transmission Electron Microscope) to observe the diameters of MNPs and the SPAnH/MNPs/Taxol magnetic nanomedicine and the distribution of SPAnH/MNPs/Taxol in cells, and use electron diffraction pattern to detect the crystallographic structures. Refer to FIG. 1(a) and FIG. 1(b). MNPs and SPAnH/MNPs respectively have diameters of 8 nm and 15 nm. Refer to FIG. 1(c). The SPAnH/MNPs nanocomposite has crystallographic planes (400), (311), (422), (220) and (440). It can prove that MNPs and SPAnH/MNPs contain $Fe_3O_4$ crystal according to JCPDS (Joint Committee on Powder Diffraction Standards).

Figure 1D:
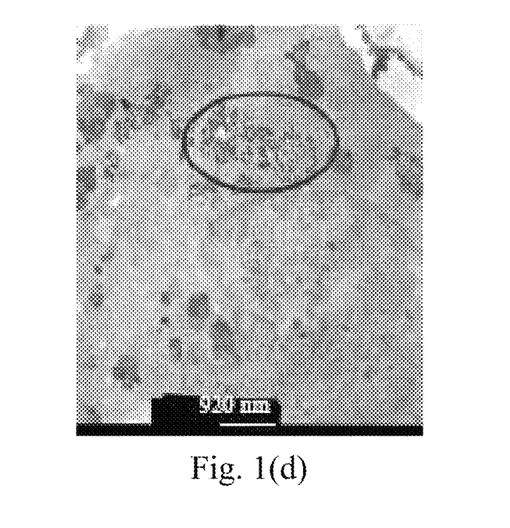
FIG. 1(d) shows a TEM photograph of PC3 prostate cancer cells at a magnifying power of 10000×.

In the case that SPAnH/MNPs/Taxol is added to the culture plates containing PC3 cancer cells, it is found: after 2 hours of cultivation, SPAnH/MNPs/Taxol enters PC3 cancer cells via pinocytosis. The crystallographic planes of the black particles inside the circle in FIG. 1(d) are respectively (400), (311), (422), (220) and (440), which are identical to those of MNPs. It can prove that the particles inside the cell indeed contain MNPs and belong to the SPAnH/MNPs magnetic nanocomposite.

The experimental result shows that the SPAnH/MNPs magnetic nanocomposite can indeed enter cells and thus can carry Taxol into cells.

Embodiment XI

Figure 1E:
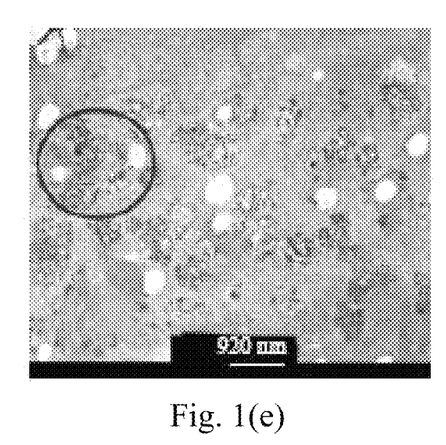
FIG. 1(e) shows a TEM photograph of CWR22R prostate cancer cells at a magnifying power of 10000×.
Figure 1F:
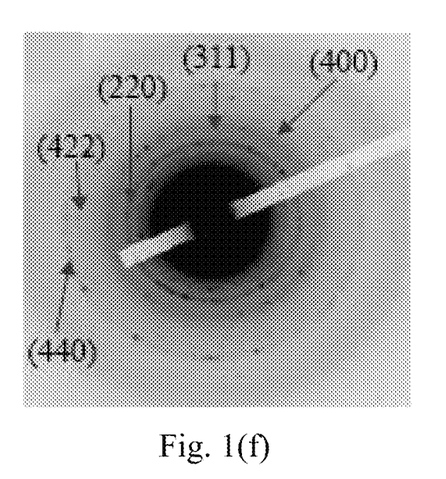
FIG. 1(f) shows an electron diffraction pattern of the areas designated by the circles in FIG. 1(d) and FIG. 1(e)

The Crystallographic Structure of the SPAnH/MNPs/Taxol Magnetic Nanomedicine in CWR22R Cancer Cells Respectively cultivate CWR22R cancer cells together with the SPAnH/MNPs nanocomposite and the SPAnH/MNPs/Taxol magnetic nanomedicine for 2 hours. Slice the samples. Use TEM (Transmission Electron Microscope) to observe the diameters of MNPs and the SPAnH/MNPs/Taxol magnetic nanomedicine and the distribution of SPAnH/MNPs/Taxol in cells, and use electron diffraction pattern to detect the crystallographic structures. Refer to FIG. 1(a) and FIG. 1(b). MNPs and SPAnH/MNPs respectively have diameters of 8 nm and 15 nm. Refer to FIG. 1(c). The SPAnH/MNPs nanocomposite has crystallographic planes (400), (311), (422), (220) and (440). It can prove that MNPs and SPAnH/MNPs contain $Fe_3O_4$ crystal according to JCPDS (Joint Committee on Powder Diffraction Standards). In the case that SPAnH/MNPs/Taxol is added to the culture plates containing CWR22R cancer cells, it is found: after 2 hours of cultivation, SPAnH/MNPs/Taxol enters CWR22R cancer cells via pinocytosis. The crystallographic planes of the black particles inside the circle in FIG. 1(e) are respectively (400), (311), (422), (220) and (440), which are identical to those of MNPs. It can prove that the particles inside the cell indeed contain MNPs and belong to the SPAnH/MNPs magnetic nanocomposite. The experimental result shows that the SPAnH/MNPs magnetic nanocomposite can indeed enter cells and thus can carry Taxol into cells.

Embodiment XII

Figure 7A:
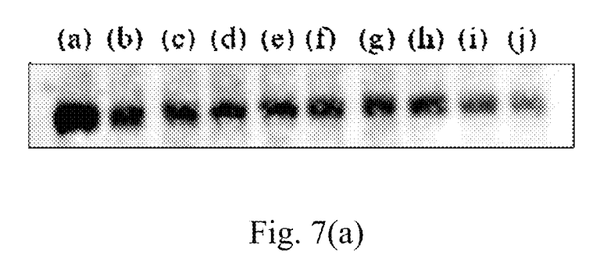
FIG. 7(a) shows the influences of different medicines on the content of α-tubulin in CWR22R prostate cancer cells.
Figure 7B:
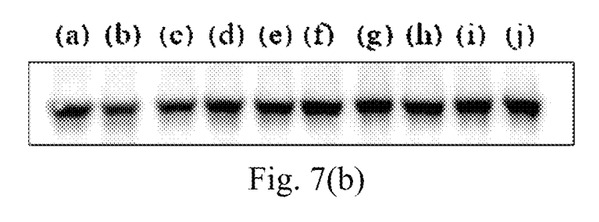
FIG. 7(b) shows the influences of different medicines on the content of β-actin in CWR22R prostate cancer cells.

The Influence of the SPAnH/MNPs/Taxol Magnetic Nanomedicine on the Content of α-Tubulin in CWR22R Prostate Cancer Cells Respectively cultivate CWR22R cancer cells together with 2, 5, 10 μM of Taxol and 2, 5, 10 μM of the SPAnH/MNPs/Taxol magnetic nanomedicine for 24 hours. Next, extract and quantify protein of cancer cells, wherein the Western method is used to analyze the content of tubulin in cellular protein. Firstly, let CWR22R cancer cells, which have reacted with Taxol or the SPAnH/MNPs/Taxol magnetic nanomedicine, respectively react with a primary antibody α-tubulin and (3-actin at a temperature of 4 C.° for 12 hours. Next, let the products react with a secondary antibody at an ambient temperature for one hour. Then, use a chemiluminescent system (ECL, Millipore Corporation, USA) and a BIO-PROFIL BIO-1D++ software to quantify the content of α-tubulin in cells. The experimental result is shown in FIG. 7. 10 μM Taxol and 10 μM SPAnH/MNPs/Taxol magnetic nanomedicine respectively have α-tubulin inhibition ratios of 52% and 63%. When a magnetic field is applied to the culture plates, the α-tubulin inhibition ratio of the SPAnH/MNPs/Taxol magnetic nanomedicine is increased to 81%.

Embodiment XIII

Figure 11:
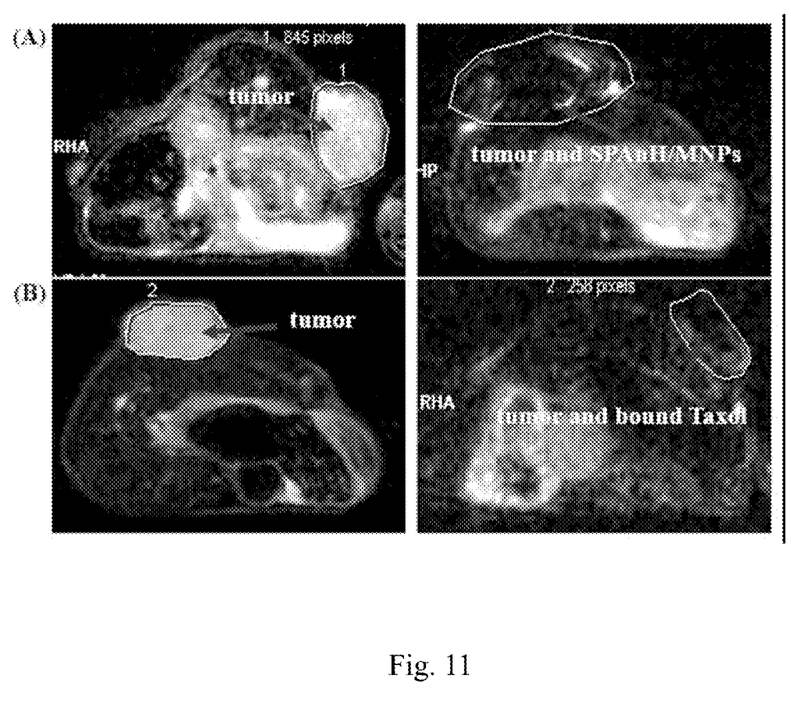
FIG. 11 shows the influences of the magnetic nanomedicine of the present invention on cancer cells in animal tests; in (A), the left photograph shows the distribution of cancer cells in nude mice before medicine injection; the right photograph shows the distribution of cancer cells in nude mice 8 days later after the magnetic nanocomposite is injected into the nude mice with an external magnetic field applied to the cancer area; in (B), the left photograph shows the distribution of cancer cells in nude mice before medicine injection; the right photograph shows the distribution of cancer cells in nude mice 8 days later after the magnetic nanomedicine is injected into the nude mice with an external magnetic field applied to the cancer area.

Using Animal Tests to Verify the Effect of the SPAnH/MNPs/Taxol Magnetic Nanomedicine on CWR22R Prostate Cancer Cells All the animal tests in the present invention were approved by the Animal Test Administration Committee. The animals used in the tests are all male Nu-Nu Balb/c mice (20-30 g). In the tests, 200 μL of phosphate solution containing $1 \times 10^7$ CWR22R cancer cells is injected into the skin of the nude mice. When the cancer grows to a size of 50-100 square millimeters ($mm^2$), the SPAnH/MNPs/Taxol magnetic nanomedicine is injected into the caudal veins to treat the mice by a dose of 6 mg Taxol/kg each two days. The mice are divided into two groups—a control group and an experimental group, and each group has three mice. The SPAnH/MNPs nanocomposite and the SPAnH/MNPs/Taxol magnetic nanomedicine are respectively injected into the mice of the control group and the experimental group, and a 2800-Gauss magnetic field is applied to the cancer areas. Refer to FIG. 11, eight days later after medicine injection, use MRI T2 images to observe the distribution of medicine and the size of cancers. The results thereof are shown in FIG. 11. In FIG. 11(A) are observed that the magnetic field applied to the cancer areas guides the SPAnH/MNPs nanocomposite to concentrate in the cancer areas, that the SPAnH/MNPs nanocomposite does not inhibit the cancers, and that the size of cancers increases by about 31.5% 8 days later after treatment. In FIG. 11(B) are observed that the magnetic field applied to the cancer areas guides the SPAnH/MNPs/Taxol magnetic nanomedicine to increase the local concentration of medicine in the cancer areas when the medicine flows through the cancers and that the size of cancers decreases by about 14.4% 8 days later after treatment.

In conclusion, the present invention bonds Taxol or its derivatives to the surface of a magnetic nanocomposite to form a magnetic nanomedicine having a diameter of 20-50 nm. The magnetic nanomedicine of the present invention is free of surfactants, dispersing agents and crosslinking agents and has higher thermal stability and water-solubility and lower biological rejection. Further, the magnetic nanomedicine of the present invention can be magnetically conducted to the cancer area to enhance the therapeutic effect without using surgical operation.

What is claimed is:

1. A magnetic nanomedicine for inhibiting/treating human prostate cancer, comprising
    a core consisting of a magnetic particle having a diameter of less than 10 nm;
    a shell made of a carboxylated polyaniline and encapsulating said core; and
    an anti-prostate cancer medicine covalently linked to said shell
    wherein said anti-prostate cancer medicine is Taxol expressed by a chemical formula:

wherein $R_1$ is benzanthracene ($C_6H_5CO$) and $R_2$ is acetyl ($CH_3CO$).

2. The magnetic nanomedicine according to claim 1, wherein said magnetic particle is made of a material selected from a group consisting of ferric ferrous oxide, ferric oxide, and nickel.

3. The magnetic nanomedicine according to claim 1, wherein said carboxylated polyaniline is expressed by a chemical formula:

wherein said —R is a functional group selected from a group consisting of —H, —COR$_1$COO$^-$, —COR$_1$COOH, —COR$_1$COOLi, —COR$_1$COONa, —COR$_1$COOK, —COR$_1$COONH$_4^+$, —COR$_1$CONH$_2$, —R$_1$COOH, —R$_1$COOLi, —R$_1$COONa, —R$_1$COOK, —R$_1$COONH$_4^+$ and —R$_1$CONH$_2$, and wherein said R$_1$ is selected from a group consisting of alkyl groups containing 2-4 carbon atoms and alkenes containing 2-4 carbon atoms, and wherein x+y<1, and x, y is not 0, and m is an integer.

4. The magnetic nanomedicine according to claim 2, wherein said carboxylated polyaniline is expressed by a chemical formula:

wherein said —R is a functional group selected from a group consisting of —COR$_1$COO$^-$, —COR$_1$COOH, —COR$_1$COOLi, —COR$_1$COONa, —COR$_1$COOK, —COR$_1$COONH$_4^+$, —COR$_1$CONH$_2$, —R$_1$COOLi, —R$_1$COONa, —R$_1$COOK, —R$_1$COONH$_4^+$ and —R$_1$CONH$_2$, and wherein said R$_1$ is selected from a group consisting of alkyl groups containing 2-4 carbon atoms and alkenes containing 2-4 carbon atoms, and wherein x+y<1, and x, y is not 0, and m is an integer.

5. The magnetic nanomedicine according to claim 1, wherein said magnetic nanomedicine has a diameter of 25-50 nm.

6. The magnetic nanomedicine according to claim 1, wherein said anti-prostate cancer medicine is bonded to said shell at a temperature of 15-20 C.°.

\* \* \* \* \*